US005723755A

United States Patent [19]
Fortin

[11] Patent Number: 5,723,755
[45] Date of Patent: Mar. 3, 1998

[54] LARGE SCALE PRODUCTION OF HUMAN OR ANIMAL PROTEINS USING PLANT BIOREACTORS

[75] Inventor: Marc G. Fortin, Ste-Anne-de-Bellevue, Canada

[73] Assignees: Francis E. Lefaivre; McGill University, both of Canada

[21] Appl. No.: 442,255

[22] Filed: May 16, 1995

[51] Int. Cl.$^6$ .............. A01H 5/00; C12N 15/12; C12N 15/82; C12N 15/84; C12N 15/24

[52] U.S. Cl. ............. 800/205; 435/69.1; 435/69.52; 435/69.6; 435/172.3; 435/240.4; 435/320.1; 435/70.1; 536/24.1

[58] Field of Search .............. 800/205; 435/69.52, 435/70.1, 172.3, 240.4, 69.1, 69.6, 320.1; 536/24.1

[56] References Cited

U.S. PATENT DOCUMENTS

| | | | |
|---|---|---|---|
| 4,956,282 | 9/1990 | Goodman et al. | 435/69.1 |
| 4,992,373 | 2/1991 | Bang et al. | 435/226 |
| 5,362,865 | 11/1994 | Austin | 536/24.1 |

OTHER PUBLICATIONS

Anson et al., 1985, *Nature*, 315:683–685.
Bradford, N.M. 1976, *Anal. Bio–chem.*, 72:248–254.
Busby et al., 1985, *Nature*, 316:271–273.
de la Salle et al., 1985, *Nature*, 316:268–270.
Dreyfus, M. et al., 1991, *N. Engl. J. Med.*, 325:1565–1568.
Grinnell et al., 1987, *Bio/Technology*, 5:1189–1192.
Hoekema et al., 1983, *Nature*, 303:179–180.
Liu et al., 1993, *Human Gene Therapy*, 4: 491–301.
McClure et al., 1992, *J. Biol. Chem.*, 267:19710–19717.
Nagel et al., 1992, *Plant Mol. Biol. Rep.*, 10:263–272.
Regneault et al., 1991, *Thromb. Res.*, 63:629–640.
Velander et al., 1991, *Ann. N.Y. Acad. Sci.*, 665:391–403.
Velander, W.H. et al., 1991, *In protein C and related anticoagulants*, Bruley, D.F. and W.N. Drohan (eds), Portfolio. The Woodlands, Texas, pp. 11–27.
Velander et al., 1992, *Proc. Natl. Acad. Sci. USA*, 89:12003–12007.
Land et al. Plant Physiol. 91: 130–135, 1989 Bacterial Chitinase is Modified and Secreted in Trausgenic Tobacco.

*Primary Examiner*—David T. Fox
*Assistant Examiner*—Thomas Haas
*Attorney, Agent, or Firm*—Klauber & Jackson

[57] ABSTRACT

The present invention relates to an expression vector for the large scale production of a human or animal protein, which comprises a DNA construct consisting of operatively linked DNA coding for a plant promoter, a transcription terminator and the human or animal protein to be expressed. Such human or animal proteins may be selected from the group consisting of human protein C (HPC), factor VIII, growth hormone, erythropoietin, interleukin 1 to 7, colony stimulating factors, relaxins, polypeptide hormones, cytokines, growth factors and coagulation factors. The present invention also relates to the plant bioreactor and to the method for the large scale production of human or animal proteins.

12 Claims, 4 Drawing Sheets pCP2 pLG3

|  U  US  S  T+  T-  T+ |
|---|

LARGE SCALE PRODUCTION OF HUMAN OR ANIMAL PROTEINS USING PLANT BIOREACTORS

BACKGROUND OF THE INVENTION

1. Field of the Invention

The invention relates to a vector for large scale production of human or animal proteins using plant cells, a method of large scale production of human or animal proteins using plant cells, to a method of large scale production of human protein C using plant cells and to plant bioreactors for the expression of human or animal proteins using plant cells.

2. Description of Prior Art

Several foreign proteins have been expressed in plants for diverse purposes: pest resistance, viral and fungal resistance, environmental stress tolerance, herbicide resistance or tolerance, food quality and processing, experimental studies, and for the expression of specialty chemicals.

Among the proteins which were expressed in plant cells, there is the following:

- A human neuropeptide which was linked to a fragment of the plant 2S albumin gene. The peptide accumulated in the seeds of Arabidopsis and of oilseed rape at levels up to 200 nmol and 50 nmol respectively per gram of seeds;
- Chicken ovalbumin in alfalfa with levels of ovalbumin up to 0.01% of total soluble proteins;
- The prepro-human serum albumin gene was transfected in potatoes. The prosequence was not cleaved before secretion from the plant cells but the human signal sequence was recognized by the plant endoplasmic reticulum; and
- Antibodies were produced in tobacco plants.

Using plant transgenics for the mass production of foreign proteins has several advantages, such as the low cost of growing the plants, the possibility of growing the transgenic plants on a very large scale, the transformation procedures which are well established, and the possibility of using specific plant parts as a sink for engineered proteins. However, in the case of human or animal proteins requiring post-translational modifications, the lack of knowledge concerning the post-translational modifications in plants represents a potential problem.

Agrobacterium-mediated gene transfer is the most widely used technique for plant transformation. *Agrobacterium tumefaciens* is a saprophytic soil bacterium which is also a pathogen of many dicotyledonous plants causing the formation of crown galls. Pathogenic Agrobacterium has a megaplasmid of approximately 200 kilo base pairs called the Ti plasmid or tumour-inducing plasmid. The T-DNA (or transferred DNA) within the megaplasmid is delimited by two 25 base-pair (bp) sequences called the right and left borders. Virulence genes are located outside the T-DNA. These contain the information for the excision of the T-DNA at the T-DNA borders, and its transfer to the plant cells. Agrobacterium-mediated gene transfer takes advantage of this system to transfer foreign DNA.

The binary vector strategy exploited here uses *E. coli*-Agrobacterium shuttle vector. This vector contains the T-DNA borders flanking the foreign DNA. This vector is introduced into Agrobacterium which moves the T-DNA in trans to the plant cells. The binary vector strategy uses disarmed Ti plasmids.

There is a demand for many human or animal proteins which have therapeutical applications. These proteins are sometimes difficult to produce in large quantities.

Since the use of human protein C (HPC) concentrate as a therapy appears promising (Dreyfus, M. et al., 1991, *N. Engl. J. Med.*, 325:1565–1568), several isolation and production systems have been studied.

The purification of HPC from human plasma constitutes a challenge since HPC is present in the plasma at concentrations of approximately 4 μg/ml and contaminants from similar vitamin K-dependent plasma proteins may be difficult to remove. In addition, there is always the possibility of infectious agent contamination. Nevertheless, Velander et al. (1991, In protein C and related anticoagulants, Bruley, D. F. and W. N. Drohan (eds), Portfolio, The Woodlands, Texas, p.11–27) designed a protocol to purify HPC from plasma. The starting material is either cryopoor plasma or reconstituted Cohn IV-1 paste which is filtered and adsorbed on an anion-exchange chromatography column. The eluate containing HPC is treated with solvent and detergent to inactivate viruses and it is adsorbed on a protein C immunoaffinity column. The eluate is again adsorbed on anion-exchange chromatography and HPC finally undergoes diafiltration before formulation. The amount of purified HPC is small and may not be useful for industrial applications.

Synthesis of biologically active recombinant protein C by bacteria or yeast is precluded because those organisms are unable to perform some of the critical post-translational modifications. Production of vitamin K-dependent plasma proteins by most mammalian cells resulted in partially processed proteins and low transcription levels (Anson et al., 1985, *Nature*, 315:683–685; Busby et al., 1985, *Nature*, 316:271–273; Grinnell et al., 1987, *Bio/Technology*, 5:1189–1192; de la Salle et al., 1985, *Nature*, 316:268–270). However, improved cell lines have been described recently, which secreted correctly processed HPC (McClure et al., 1992, *J. Biol. Chem.*, 267:19710–19717). The best results have been achieved using transgenic animals. Velander et al. (1991, *Ann. N.Y. Acad. Sci.*, 665:391–403) demonstrated that engineered mice could produce biologically active HPC in their milk at concentrations of up to 3 μg/ml. Velander et al. (1992, *Proc. Natl. Acad. Sci. USA*, 89:12003–12007), also reported that transgenic swine were capable of high-level expression of HPC. A concentration of 1 g per liter of milk was detected from the best animal. The use of animals for the production of human protein C is not desirable due to the difficulties associated with the purification of the human transgenic protein away from related animal proteins.

It would be highly desirable to be provided with a vector for the large scale production of human or animal proteins using plant cells.

It would be highly desirable to be provided with a bioreactor for the large scale production of human or animal proteins using plant cells.

It would be highly desirable to be provided with a method of large scale production of human or animal proteins using plant cells.

It would be highly desirable to be provided with a method of large scale production of human protein C using plant cells.

SUMMARY OF THE INVENTION

One aim of the present invention is to provide a vector for the large scale production of human or animal proteins using plant cells.

Another aim of the present invention is to provide a method of large scale production of human or animal proteins using plant cells.

Another aim of the present invention is to provide a bioreactor for the large scale production of human or animal proteins using plant cells.

Another aim of the present invention is to provide a method of large scale production of human protein C using plant cells.

In accordance with one embodiment of the present invention, there is provided an expression vector for the large scale production of a human or animal protein, which comprises a DNA construct consisting of operatively linked DNA coding for a plant promoter, a transcription terminator and said human or animal protein to be expressed. More specifically, the expression vector is referred to as pCP2.

In accordance with another embodiment of the present invention, there is provided an expression vector for the large scale production of a human or animal protein, which comprises a DNA construct consisting of operatively linked DNA coding for a plant promoter, a mRNA stabilizer, a transcription terminator, and said human or animal protein to be expressed. More specifically, the expression vector is referred to as pLG3.

In accordance with the present invention there is provided a plant bioreactor for the large scale production of a human or animal protein, which comprises dicotyledonous plants transformed with a DNA construct consisting of operatively linked DNA coding for a plant promoter, a transcription terminator and said human or animal protein to be expressed flanked by T-DNA borders and a suitable selectable marker for plant transformation.

In accordance with the present invention there is provided a plant bioreactor for the large scale production of a human or animal protein, which comprises dicotyledonous plants transformed with a DNA construct consisting of operatively linked DNA coding for a plant promoter, a mRNA stabilizer, a transcription terminator and said human or animal protein to be expressed flanked by T-DNA borders and a suitable selectable marker for plant transformation.

In accordance with the present invention there is provided a method of large scale production of human or animal proteins, which comprises the steps of:

a) inserting a suitable recombinant expression vector in plant cells using Agrobacterium transformation, said expression vector comprising operatively linked DNA coding for a plant promoter, a transcription terminator and said human or animal protein to be expressed flanked by T-DNA borders and a suitable selectable marker for plant transformation; and b) recovering said expressed human or animal protein of step a) from said culture medium.

In accordance with the present invention there is provided a method of large scale production of human or animal proteins, which comprises the steps of:

a) inserting a suitable recombinant expression vector in plant cells using Agrobacterium transformation, said expression vector comprising operatively linked DNA coding for a plant promoter, a mRNA stabilizer, a transcription terminator and said human or animal protein to be expressed flanked by T-DNA borders and a suitable selectable marker for plant transformation; and b) recovering said expressed human or animal protein of step a) from said culture medium.

In accordance with the present invention there is provided a method of large scale production of human protein C, which comprises the steps of:

a) inserting a suitable recombinant expression vector in plant cells using Agrobacterium transformation, said expression vector comprising operatively linked DNA coding for a plant promoter, a transcription terminator and said human protein C to be expressed flanked by T-DNA borders and a suitable selectable marker for plant transformation; and b) recovering said expressed human protein C of step a) from said culture medium.

In accordance with the present invention there is provided a method of large scale production of human protein C, which comprises the steps of:

a) inserting a suitable recombinant expression vector in plant cells using Agrobacterium transformation, said expression vector comprising operatively linked DNA coding for a plant promoter, a mRNA stabilizer, a transcription terminator, and said human protein C to be expressed flanked by T-DNA borders and a suitable selectable marker for plant transformation; and b) recovering said expressed human protein C of step a) from said culture medium.

For the purpose of the present invention the following terms are defined below.

The term "human or animal proteins" is intended to mean any human or animal protein which include without limitation, human protein C (HPC), factor VIII, growth hormone, erythropoietin, interleukin 1 to 7, colony stimulating factors, relaxins, polypeptide hormones, cytokines, growth factors and coagulation factors.

The term "plants" is intended to mean any dicotyledonous plants, which include without limitation tobacco, tomato, potato, crucifers.

The term "operatively linked" is intended to mean that the elements are physically joined on the same piece of DNA to produce a unit with a specific purpose.

The term "T-DNA borders" is intended to mean the 25 base pair Agrobacterium-derived sequences that delimit the fragment of DNA that will be transferred to the plant cell with the help of Agrobacterium proteins.

The expression "a suitable selectable marker for plant transformation" is intended to mean any gene coding for a function that will allow the identification of transformed plant cells, such as kanamycin resistance.

BRIEF DESCRIPTION OF THE DRAWINGS

FIG. 7 illustrates a Western immunoblot of reduced samples from ion-exchange #7 using a rabbit anti-HPC serum.

DETAILED DESCRIPTION OF THE INVENTION

Figure 1:
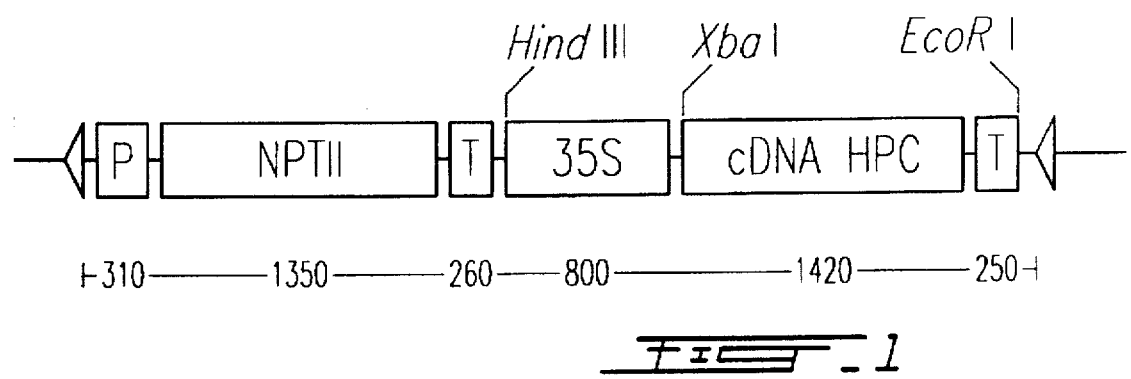
FIG. 1 illustrates the construction of plasmid pCP2.

The present invention was designed to express human or animal proteins, namely human protein C (HPC), in plants. This novel approach has several advantages over mammalian transgenics: the low cost of growing the plants, the ability to produce the protein on a very large scale, and the elimination of contamination by related animal proteins during purification of the expressed human or animal protein.

The preferred biorectors in accordance with the present invention include most dicotyledonous plants, particularly the solonacae, which include (but are not limited to) tobacco, potato and tomato, and the crucifers as transformed with the vector of the present invention.

The preferred plants in accordance with the present invention include without limitation tobacco, tomato, potato and crucifers.

Many other human or animal proteins, beside human protein C, may be prepared in accordance with the present invention. The preferred human or animal proteins to be expressed in accordance with the present invention include, but are not limited to, anticoagulation proteins, such as human protein C, factor VIII, or tissue plasminogen activator, and other proteins of pharmaceutical or veterinary interest.

Human protein C (HPC) is a vitamin K-dependent plasma glycoprotein which is a key element of the anticoagulation cascade. It is synthesized by the liver cells as a single peptide but is modified into a heterodimer linked by a disulfide bond before its secretion to the bloodstream. Some individuals are partially or completely HPC deficient, a situation that increases the likelihood of an early thrombotic event which may be lethal. Purified HPC injection has been used as an experimental treatment for homozygous deficient patients who are not producing HPC, but is also a promising drug for several other complications such as septic shock, thrombolytic therapy, and hip replacement. The annual demand in the U.S.A. for HPC represents about 96 kg. At the moment, HPC is purified from human plasma. Several researchers are experimenting with the synthesis of HPC in the milk of transgenic animals. In accordance with the present invention, the production of HPC is intended to serve as an example of the human or animal proteins which can be produced at a very large scale using plants as bioreactors.

The method of the present invention involved engineering tobacco plants using Agrobacterium-mediated gene transfer associated with the binary vector strategy of Hoekema et al. (1983, *Nature*, 303:179–180). Agrobacterium-mediated gene transfer takes advantage of the gene transfer system provided by the bacterium. The binary vector strategy consists of using *A. tumefaciens* with a Ti plasmid, inserting an accessory plasmid called the binary vector into the bacterium, and allowing T-DNA transfer. The accessory plasmid contains T-DNA border sequences with the desired genes and regulating elements located between them.

Engineering tobacco plants to produce human or animal proteins, or for example HPC, was achieved via the use of either of the two plasmids with different elements for the regulation of the expression of the introduced cDNA. The first plasmid included the constitutive cauliflower mosaic virus (CaMV) 35S promoter to drive gene expression, the second included a dimer of the 35S constitutive promoter with an alfalfa mosaic virus (AMV) leader sequence to enhance stability of the transcript. Duplicating the promoter has previously been found to enhance transcription, while the leader sequence enhanced translation.

Expression of the T-DNA was verified by analyzing HPC and neomycin phosphotransferase II (NPTII) synthesis by enzyme linked immunosorbent assay (ELISA) and inheritance of the T-DNA insert was observed by germinating $R_1$ seeds on antibiotic-containing medium or by ELISA to HPC on $R_1$ seedlings.

Purification protocols were created and preliminary experiments are described. Biological activity of various protein fractions was measured.

Tobacco plants engineered with the human protein C (HPC) cDNA and plant promoters expressed HPC. This was demonstrated by ELISA and Western assays using a combination of antibodies to human protein C. No similar protein was found in non-transformed plants. The protein had the expected molecular weight of the uncleaved form of HPC.

Changes in coagulation times were observed in several experiments when tobacco extracts were tested for clotting activity.

Plant transformation and selection

Several cell types or tissues can be used but cells must be totipotent, that is, able to regenerate mature plants. Plant cells or tissues are co-cultivated with Agrobacterium for a few days to allow T-DNA transfer. After co-cultivation, plant cells and tissues are grown on media with antibiotic which suppresses bacterial growth. Engineered plant cells survive because an antibiotic resistance marker gene is transferred with the foreign DNA. This system allows elimination of non-transformed plant cells. Plantlets are regenerated for analysis using plant tissue culture media with various plant growth regulator levels.

HPC structure and post-translational modifications

HPC is a complex vitamin K-dependent plasma glycoprotein. The HPC mRNA codes for a single peptide including a signal peptide and a propeptide sequence. After cleavage of the single chain by removal of the KR dipeptide (Lys-Arg), HPC is secreted to the bloodstream as a two-chain glycoprotein with a molecular weight of 62,000 Da. The light chain (21,000 Da) and the heavy chain (41,000 Da) remain attached by a disulfide bond. However, before secretion, HPC must undergo several post-translational modifications.

Determination of HPC's biological activity

A cDNA clone coding for HPC was inserted downstream of the CaMV 35S promoter and of a dimer of the CaMV 35S promoter. Tobacco plants were transformed using Agrobacterium and a binary vector strategy. Kanamycin resistant plants were regenerated. T-DNA integration was tested to insure that plants were stably transformed. $R_1$ seedlings were also analyzed. A second round of transformation was performed in order to increase the level of HPC expression. Partial protein purification (using ion-exchange chromatography), dialysis and ultrafiltration were followed by various analyses (SDS-PAGE, Western immunoblot) in order to assess protein purity and activity. Clotting assays were performed in order to determine whether the plant-produced HPC was biologically active.

1. Recombinant DNA manipulations

The binary vector pBI121 and a culture of *Agrobacterium tumefaciens* strain LBA4404 were purchased from Clontech. The plasmid pBI524 and pLPC were provided by Dr. Bill Crosby from Agriculture Canada and by Dr. Jeff Turner (Department of Animal Science, McGill University). Restriction and modifying enzymes were purchased from New England Biolabs and the DNA marker (1KB DNA ladder) from BRL. Standard recombinant DNA manipulations were used during the construction of the binary vectors and all plasmid manipulations were performed using *E. coli* strain DH5α if not specified. Finally, the concentration of agarose for gel electrophoresis was 0.8% unless mentioned, and gels were run in 0.7X TBE buffer (89 mM Tris, 89 mM boric acid, 2 mM EDTA, pH 8.3). Specific DNA fragments to be recovered after enzymatic digestion were electrophoresed in TAE buffer (40 mM Tris-acetate, 2 mM Na$_2$EDTA, pH 8.5) and the Geneclean™ II kit (BiO 101) was used to purify and extract the DNA from the agarose gel.

1.1 Non-radioactive hybridization

Plasmid DNA was digested with XbaI and EcoRI, electrophoresed in 1% agarose gels (TBE), and transferred onto Hybond™ N⁺ nylon membrane (Amersham) by alkaline transfer with 0.4M NaOH according to the membrane manufacturer's instructions. The BclI fragment containing the HPC cDNA from pLPC was digested, electrophoresed in an agarose gel in TAE, and isolated by Geneclean™ II. The BclI fragment was used as the probe. Probe labelling, hybridization, and detection was carried out using non-radioactive DIG™ DNA Labelling and Detection Kit (Boehringer Mannheim) according to the manufacturer's instructions.

1.2 Genomic DNA isolation

Plant genomic DNA from transgenic tobacco was isolated using the CTAB (hexadecyltrimethylammonium bromide) method. Five grams of leaf material (previously frozen at −70° C.) were homogenized in 15 ml of prewarmed CTAB buffer (100 mM Tris-Cl pH 8.0, 1.4M NaCl, 20 mM EDTA, 0.2% β-mercaptoethanol, 2% CTAB) in a Waring™ blender and incubated for 30 minutes at 60° C. The solution was mixed every 5 minutes. An equal volume of chloroform-isoamyl alcohol (24:1) was added to the tube, mixed well and centrifuged 3000 g for 15 minutes at 4° C. The aqueous phase was collected and chloroform-extracted once more. The aqueous phase was transferred to a new tube and precooled (−20° C.) isopropanol was added ⅔ volume of the aqueous solution. The mixture was inverted a few times and incubated at −20° C. for at least 60 minutes. DNA was precipitated by centrifugation 10,000 g for 10 minutes at 4° C. Supernatant was removed and the DNA pellet washed with 10 mM ammonium acetate in 76% ethanol. DNA was vacuum-dried and resuspended in TE buffer (10 mM Tris-Cl and 1 mM EDTA, pH 8.0).

1.3 Southern hybridization

Genomic DNA (20 μg) was digested with Sau3AI and DNA fragments were separated by agarose gel electrophoresis (1% agarose) in TBE buffer. DNA was transferred to Hybond™ N⁺ nylon membrane (Amersham) using alkaline transfer following the manufacturer's instructions. The DNA probe was the cDNA of HPC (BclI fragment of pLPC) labelled with $\alpha^{32}$P-dCTP (ICN) using the T7 Quickprime™ kit of Pharmacia. The nylon membrane was incubated in 30 ml of prehybridization buffer (250 mM NaHPO$_4$ pH 7.2, 2.5 mM EDTA, 7% sodium dodecyl sulfate (SDS), 1% blocking reagent (Boehringer Mannheim), 50% deionized formamide) for 24 hours at 42° C. The prehybridization buffer was replaced by 15 ml of hybridization buffer (prehybridization buffer with 10% dextran sulfate) and incubated with the probe and the membrane overnight at 42° C. The membrane was washed three times 15 minutes at 42° C. with 2X SSC (20X SSC was 3M NaCl and 0.3M Na$_3$citrate, pH 7.0) and 0.1% SDS, followed by 0.5X SSC and 0.1% SDS, and then 0.1X SSC and 0.1% SDS. The final wash was with 0.1X SSC and 0.1% SDS for 30 minutes at 52° C. The X-ray film (Kodak™ X-OMAT AR) was exposed for approximately 7 days.

1.4 Transfer of plasmids into Agrobacterium

Three plasmids (pBI121, pCP2, and pLG3) were purified from *E. coli* using an alkaline lysis DNA minipreparation. Vector DNA was transferred to *A. tumefaciens* strain LBA4404 using a freeze and thaw method.

2. Plant transformation

2.1 Plant material propagation

Seeds of *Nicotiana tabacum* cv. Xanthi were sterilized for 15 minutes in a 10% bleach solution with a drop of detergent (Tween™-20). Seeds were washed at least five times with sterile distilled water and allowed to germinate and grow on artificial medium composed of basal MS salts, B5 vitamins, 3% sucrose, and 0.6% agar (Anachemia) at pH 5.7–5.8. Seed were grown under a 16 hour photoperiod with a light intensity of 50 μE and a temperature of 24° C.

2.2 Preparation of Agrobacterium inoculum

*A. tumefaciens* was grown in Luria Broth (LB) (1% tryprone, 0.5% yeast extract, 85 mM NaCl, pH 7.0) medium supplemented with 50 μg/ml kanamycin and 25 μg/ml of streptomycin for 18 hours or until the optical density at 595 nm reached 0.5 to 1.0. Cells were spun down at 3,000 g for 5 minutes and the pellet was resuspended to its initial volume with MS-104 medium (MS basal salts, B5 vitamins, 3% sucrose, 1.0 μg/ml benzylaminopurine (BAP), 0.1 μg/ml naphtaleneacetic acid (NAA), pH 5.7–5.8, and 0.8% agar) without agar.

2.3 Leaf disc transformation

Leaf squares of about 64 mm² were dissected using a sharp scalpel, immersed in the inoculum for 15–30 minutes and plated onto MS-104 medium for 2 days under a 16 hour photoperiod, under low light intensity (20 μE) at 24° C. for cocultivation. Leaf discs were washed alternately three times with sterile distilled water for 1 minute and sterile distilled water supplemented with 500 μg/ml of carbenicillin for 5 minutes. Leaf discs were transferred to MS-104 medium with 500 μg/ml of carbenicillin for another 2 days under the same environmental conditions.

2.4 Selection and regeneration

Leaf discs were washed as above, plated on MS-104 medium with 500 μg/ml of carbenicillin and 100 μg/ml of kanamycin, and grown using the above environmental conditions until calluses appeared. The light intensity was increased to 50 μE and the explants were allowed to grow until development of well-formed shoots. Shoots were excised and transferred onto MS-rooting medium (MS-104 but with 0.6% agar and no plant growth regulators) with 500 μg/ml of carbenicillin and 100 μg/ml of kanamycin. Surviving plantlets with well-formed roots were removed from the artificial medium, dipped alternately in a 0.06% 50WP Benlate™ solution and in a rooting powder (Stim-root #1) containing indole-3 butyric acid, and transplanted into pasteurized Promix™ soil mixture. Plantlets were covered with a transparent cover which was gradually lifted during the following 7 days.

3. T-DNA expression analysis

3.1 NPTII immunoassay

A double antibody sandwich enzyme linked immunosorbent assay (DAS-ELISA) was used to analyze T-DNA expression. The DAS-ELISA for NPTII detection was based on the Nagel et al. (1992, *Plant Mol. Biol. Rep.*, 10:263–272) procedure. Approximately 100 mg of leaf material was homogenized in 300 μl of PBS-TP (137 mM NaCl, 43 mM Na$_2$HPO$_4$, 27 mM KCl, 14 mM KH$_2$PO$_4$, 0.05% Tween™-20, 2% polyvinylpyrrolidone (PVP), pH 7.4). Debris was removed by centrifugation (10,000 g for 2 minutes) and the concentration of soluble proteins was determined for every sample using the Bradford method (Bradford, N. M. 1976, *Anal. Bio. Chem.*, 72:248–254). Samples were diluted to 400 μg/ml in PBS-TP. Microtiter plates (Falcon) were coated with 200 μl of rabbit anti-NPTII (5 Prime→3 Prime Inc.) diluted 1:500 in carbonate buffer (35 mM NaHCO$_3$, 15 mM Na$_2$CO$_3$, pH 9.6). The antibody was incubated for 2 hours at 37° C. Wells were washed five times with PBS-T (PBS-TP without PVP) by alternately filling the wells with a multichannel pipette and emptying the plates in the sink. Wells were blocked with a solution of PBS-T containing 2% BSA for 30 minutes at room temperature (RT). Wells were washed five more times. Leaf samples (200 μl) were added and incubated for 2 hours at RT. Wells were washed five times and 200 μl of biotinylated NPTII antibody (5 Prime→3 Prime Inc.), diluted 1:500 in PBS-TPO (PBS-TP with 0.2% BSA), was added and incubated at RT for 1 hour. Wells were washed five times and 200 μl of P-nitrophenyl phosphate (PNP) diluted to 1 mg/ml in substrate buffer (9.7% diethanolamine, pH 9.8) was incubated for approximately 40 minutes. Absorbance was measured by a microtiter plate reader (Bio-Rad™ 450) with a 405 nm filter.

3.2 HPC immunoassay

Plant samples were homogenized as for the NPTII ELISA. A polyclonal rabbit anti-HPC (Sigma) was diluted 1:2000 in carbonate buffer and used to coat the wells of microtiter plates (Falcon) for 2 hours at 37° C. Wells were washed five times with PBS-T and blocked with a solution of PBS-T and 2% BSA for 30 minutes at RT. Wells were washed five more times and 200 μl of leaf extract was added and incubated overnight at 4° C. Wells were washed five times and 200 μl of a polyclonal goat anti-HPC (Biopool), diluted 1:2000 in PBS-TPO, was added and incubated at RT for 2 hours. Wells were washed five times and 200 μl of a swine anti-goat IgG (Cedarlane), diluted 1:3000 in PBS-TPO, was added and incubated at RT for 1 hour. Wells were washed five more times and 200 μl of 1 mg/ml PNP dissolved in substrate buffer was added. Color development was allowed to proceed in the dark for at least 1 hour and color intensity was measured using a microtiter plate reader with a 405 nm filter. A standard curve was also made using purified HPC (American Diagnostica) diluted in PBS-T.

3.3 Germination of $R_1$ seeds on kanamycin-containing medium

Seeds produced by $R_0$ plants were collected and germinated on artificial medium (see described in section 2.1) containing 100 μg/ml of kanamycin to assay for antibiotic resistance among the $R_1$ generation and segregation of the transferred gene.

3.4 Double transformation $R_1$ seeds from S-2B transformed tobacco plant were grown in vitro and transformed using the pCP2 vector inserted in Agrobacterium tumefaciens (as described in section 2. above).

A total of three S-2B controls (transformed once) and 104 potentially double transformant plants were analyzed for their HPC production. DAS-ELISA was used to determine HPC concentration (using PBS-T as a blank) while the Bradford method was used to measure the soluble protein concentration (the latter analysis was made with the Bio-Rad™ protein assay kit using ddH$_2$O as a blank).

$$HPC \text{ production } [\%] = \frac{DAS\text{-}ELISA \ (HPC)}{Bradford \ (soluble \ proteins)} \times 100\%$$

4. Engineering tobacco for the expression of protein C

The tobacco genome was modified in order to synthesize HPC. This involved the construction of two plasmids which contained a T-DNA and the HPC cDNA, the transfer of HPC cDNA into tobacco and the analysis of T-DNA expression among regenerated plants.

4.1 Binary vectors

Figure 2:
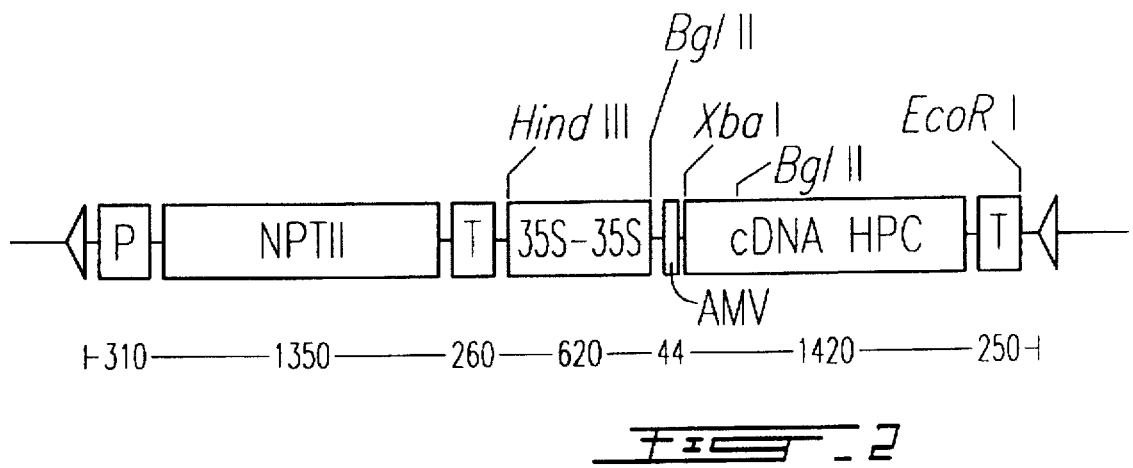
FIG. 2 illustrates the construction of plasmid pLG3.
Figure 3:
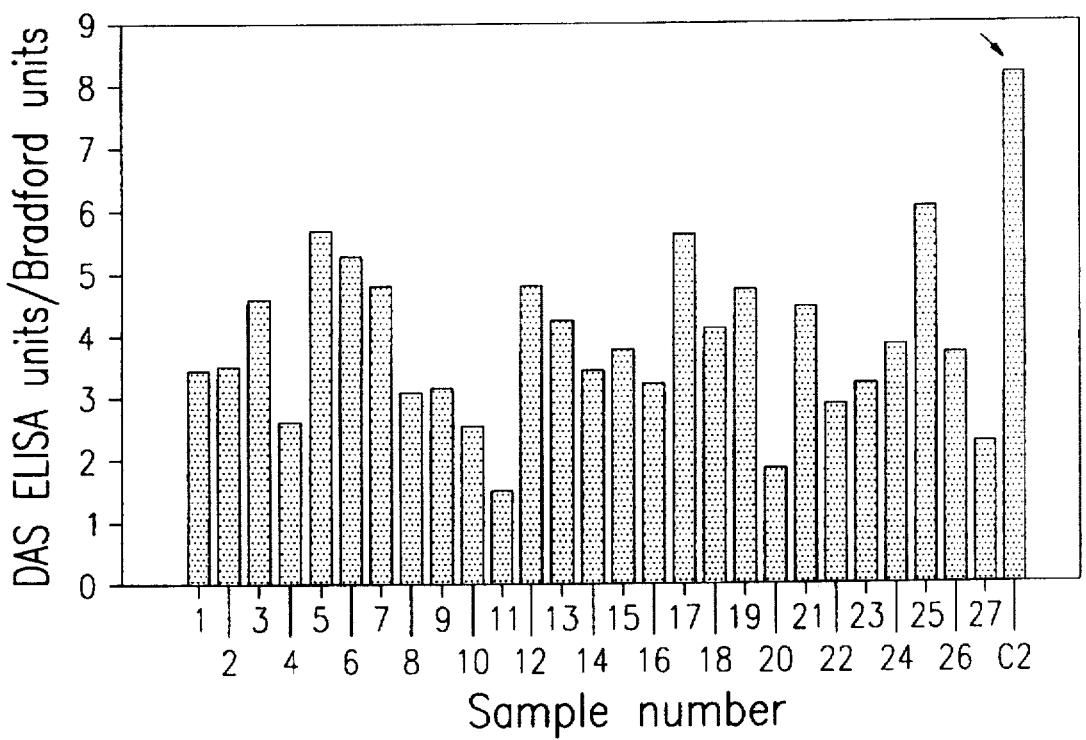
FIG. 3 is a graph of first screen for HPC production of samples 1 to 27.
Figure 4:
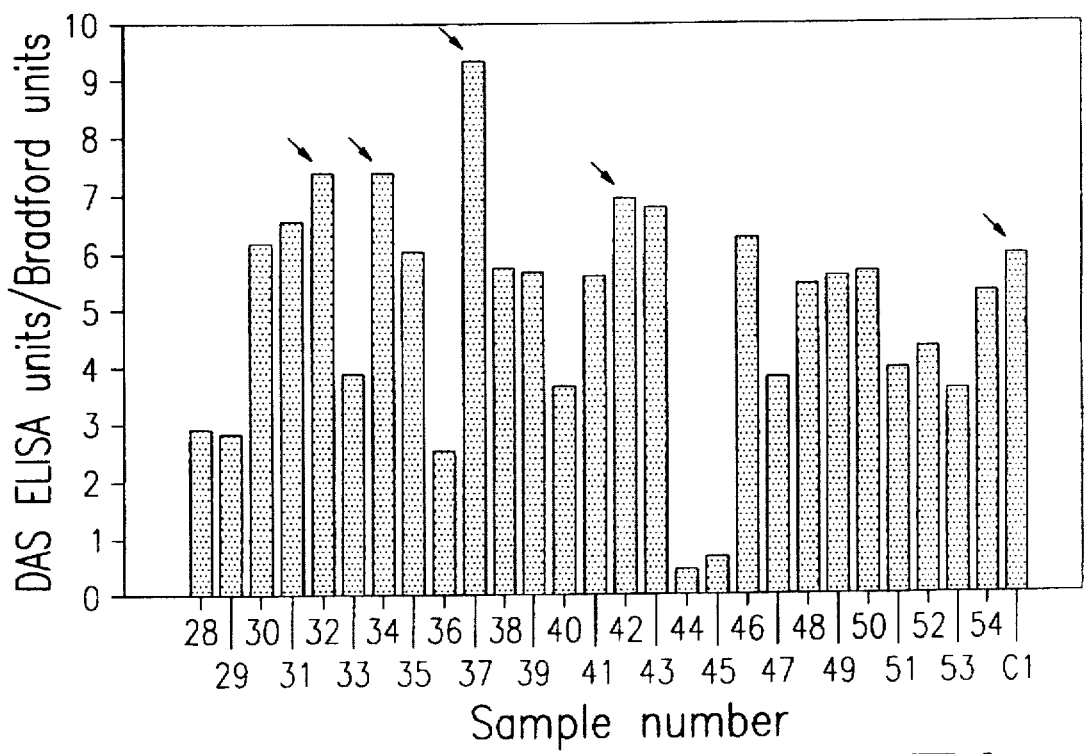
FIG. 4 is a graph of first screen for HPC production of samples 28 to 54.
Figure 5:
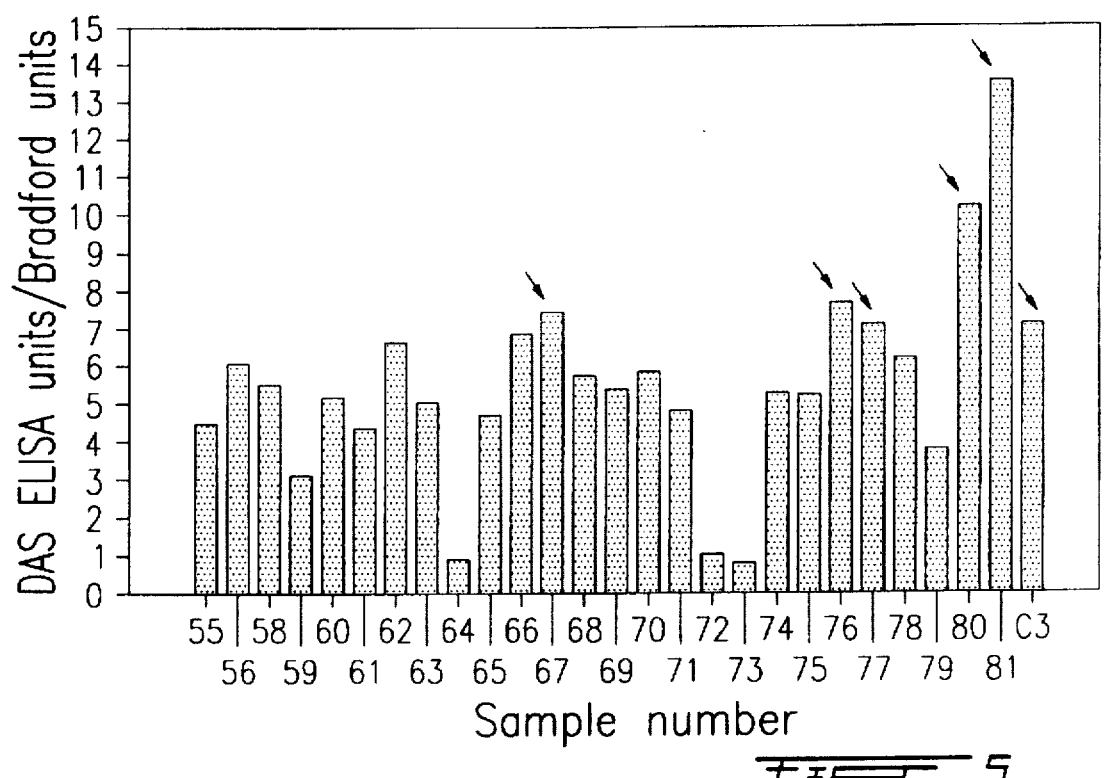
FIG. 5 is a graph of first screen for HPC production of samples 55 to 81.
Figure 6:
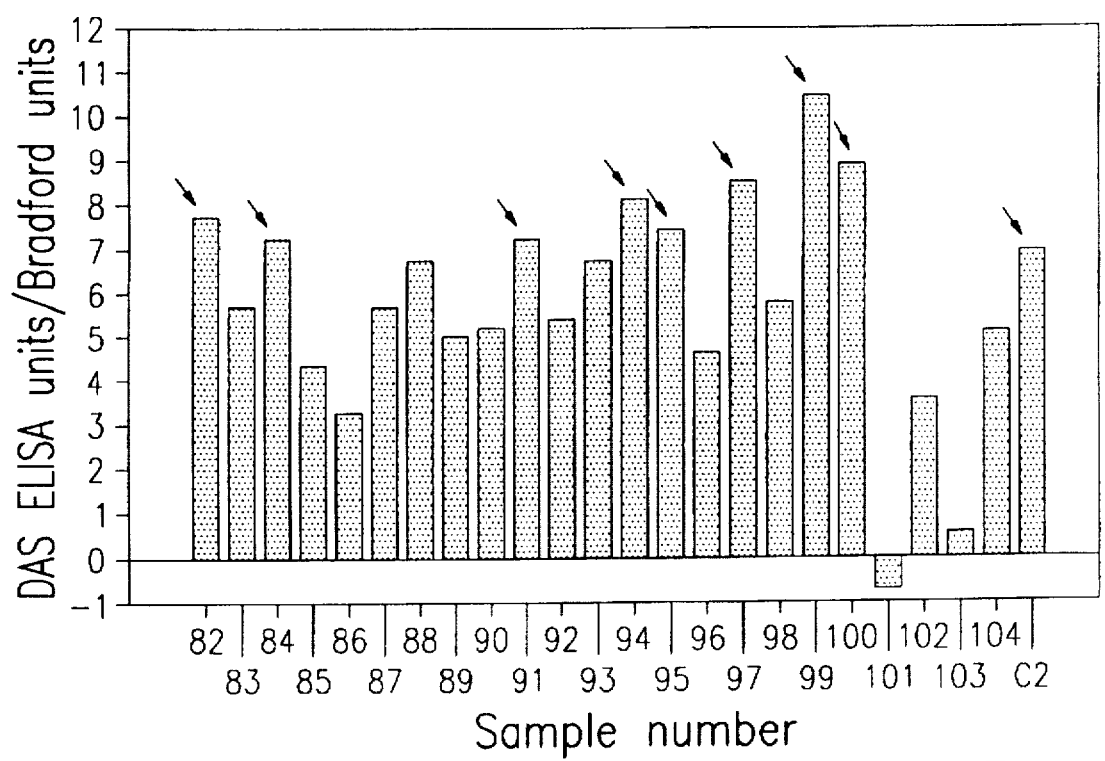
FIG. 6 is a graph of first screen for HPC production of samples 82 to 104.

Two binary vectors for the expression of plant HPC were constructed in order to avoid using a single construct which could have errors acquired during DNA manipulations. Both pCP2 (FIG. 1) and pLG3 (FIG. 2) constructs contained the right and left T-DNA border sequences and the selectable marker gene NPTII, which provides resistance to kanamycin and allows quick selection of engineered plants.

Plasmid pCP2 is a derivative of pBI 121. Its T-DNA is delimited by two T-DNA border sequences (triangles, FIG. 1) which flank the selectable marker gene neomycin phosphotransferase II (NPTII) preceeded by the nopaline synthase promoter (P) and terminated with the nopaline synthase terminator (T). In addition, the cDNA of HPC (cDNA HPC) was cloned in between the CaMV 35S promoter (35S) and a nopaline synthase terminator (T). Approximate sizes of the elements between the border sequences are indicated and key restriction sites are indicated above the diagram.

Plasmid pLG3 is a derivative of pBI 121. Its T-DNA is delimited by two T-DNA border sequences (triangles, FIG. 2)) which flank the selectable marker gene neomycin phosphotransferase II (NPTII) preceeded by the nopaline synthase promoter (P) and terminated with the nopaline synthase terminator (T). In addition, the cDNA of HPC (cDNA HPC) was cloned downstream of a double CaMV 35S promoter (35S) and an AMV leader sequence and upstream of a nopaline synthase terminator (T). Approximate sizes of the elements between the border sequences are indicated and key restriction sites are indicated above the diagram.

The NPTII gene is regulated by the nopaline synthase promoter and the NOS-T.

pCP2 construct

A 1420 bp BclI fragment, which contained the cDNA of HPC, was cut out from pLPC and cloned into the BamHI site of vector pBI524. pBI524 is a derivative of pUC9 with, (5' to 3'), a dimer of the CaMV 35S promoter, an alfalfa mosaic virus (AMV) leader sequence, a polylinker (NcoI, XbaI, BamHI), and a NOS-T. The new construct was called pCP1. The cDNA sequence was preferred to the genomic sequence because it is easier to manipulate smaller DNA sequences, and it is not known if plant cells will correctly splice out human introns.

In order to verify the-orientation of the cloned HPC cDNA, a BglII restriction digestion was performed on plasmid DNA isolated from recovered E. coli colonies. BglII was expected to cleave at the 3' end of the double CaMV 35S promoter and 210 bp away from the 5' end of HPC cDNA thus generating two DNA fragments of approximately 300 bp and 4800 bp if the cDNA was well oriented, that is the ATG codon from the HPC cDNA was immediately downstream of the AMV leader sequence. Two bands of the correct size were observed.

An XbaI-EcoRI cassette was isolated from pCP1 and ligated in place of the XbaI-EcoRI cassette from pBI121. Therefore, the GUS gene with the NOS-T was replaced by the cDNA of HPC with its accompanying NOS-T forming the plasmid pCP2. The HPC cDNA is under the control of the constitutive CaMV 35S promoter from pBI121 which is known to highly express foreign proteins.

pLG3 construct

Vector pBI524 contained an undesirable ATG which is part of the NcoI restriction site. The ATG was deleted by cleaving pBI524 with NcoI, removing single stranded sticky ends with mung bean nuclease, and ligating the modified vector which was named pLG1. The removal of the NcoI restriction site was verified with a double digestion with NcoI and ScaI. Two bands were observed when pBI524 was digested with the two restriction enzymes while only one band appeared for pLG1 indicating that the NcoI site was missing.

The HPC cDNA BclI fragment was cloned into the BamHI site of pLG1 to create pLG2. Then, a HindIII-EcoRI cassette from pLG2 was cloned in place of the HindIII-EcoRI from pBI121. Therefore, the CaMV 35S promoter along with the GUS gene and a NOS-T were replaced by a dimer of the CaMV 35S promoter with an AMV leader sequence, the cDNA of HPC, and a NOS-T. Doubling the CaMV 35S promoter is known to markedly increase transcription, while the leader sequence enhances translation of the expressed protein.

Transfer of Plasmids pCP2 and pLG3 into *A. tumefaciens*

Plasmids pCP2 and pLG3 were transferred into *A. tumefaciens* LBA4404 using a freeze/thaw method. In order to verify whether the plasmids were successfully transferred, a non-radioactive Southern hybridization was attempted. The cDNA of HPC was observed to hybridize to plasmid DNA isolated from *A. tumefaciens* and *E. coli* transfected with pCP2 while there was no hybridization with the control plasmid pBI121.

4.2 Engineering tobacco and selection of transformants

Leaf discs were inoculated with four Agrobacterium inocula:

A) Seventy-five leaf discs were inoculated with LBA4404 without any binary vector. Half of the leaf discs were grown on kanamycin-containing medium in order to verify the efficacy of kanamycin selection while the other half were grown on medium without antibiotic in order to recover negative control plants (untransformed tobacco).

B) One hundred leaf discs were inoculated with LBA4404 with the binary vector pBI121 as a control to monitor the transformation procedure's efficiency.

C) Two hundred leaf discs were inoculated with LBA4404 with the binary vector pCP2 for the expression of HPC.

D) Two hundred leaf discs were inoculated with LBA4404 with the binary vector pLG3 for the expression of HPC.

Kanamycin repressed regeneration of leaf discs inoculated with Agrobacterium without binary vector when cultivated on kanamycin-containing medium. Thus, the antibiotic selection was efficient in removing untransformed plants. Thirty-six plants were kanamycin resistant and survived transplantation to the greenhouse following inoculation with the binary vector pBI121. This indicates that the T-DNA transfer took place. A total of 230 kanamycin-resistant plants were regenerated: 118 engineered with pCP2 and 112 engineered with pLG3.

4.3 Analysis of HPC and NPTII expression

Screening $R_0$ plants for HPC expression

A DAS-ELISA procedure was preferred to other ELISA methods because this type of assay is less susceptible to non-specific binding of antibodies. Two polyclonal antibodies for HPC were selected for the sandwich complex with the HPC antigen because polyclonal antibodies recognize several epitopes of HPC. The ELISA for HPC was used to screen all recovered plants engineered with the pCP2 and pLG3 binary vectors, and to find which $R_0$ plants were potentially highly expressing HPC. A dilution of 1:2,000 was used for coating the rabbit anti-HPC antibody and 1:1,000 for the goat anti-HPC antibody. The dilution of swine anti-goat IgG was 1:3,000 as recommended by the manufacturer. Finally, the concentration of soluble protein in sap extracts was adjusted to 1 mg/ml. Negative control plants had ELISA values, after the background was removed, (PBS-TP buffer in place of sap extract) ranging from −0.003 to 0.125 with an average of 0.061 (n=38). Results for engineered plants varied from 0.025 to 0.513. All plants with ELISA values above 0.375 were selected for the optimization of the ELISA conditions and for the accurate quantification of HPC expression.

Optimization of HPC DAS-ELISA

Prior to the final HPC quantification, different ELISA conditions were tested in order to optimize the assay. Dilutions of the rabbit anti-HPC antibody and of the swine anti-goat IGg were kept as before while a 1:2,000 dilution of the goat anti-HPC antibody was used since reducing the quantity of antibody was found to only slow down color development. Eight concentrations of sap extract were tested: 1,000, 500, 250, 125, 63, 32, 16, and 8 µg/ml and the quantity of HPC present was determined using purified HPC. Overall, the percentage of HPC increased with the dilution of the sap extract (Table 1). Sap was extracted from six plants which had ELISA readings greater than 0.375 during HPC screening. Numbers represent the percentage of plant-produced HPC among total soluble proteins. ELISA readings were blanked against sap of non-transformed plants and the percentage of HPC determined against a purified HPC standard curve. A protein concentration of 5 µg/ml was selected because a lower concentration of soluble protein would be too close to the lower limit of detection and a higher concentration would lead to underestimation of the amount of HPC present.

TABLE 1

Determination of optimal soluble protein concentration in sap extractions for the immunodetection of HPC

| µg/ml leaf extract | S2F | SS4B | SS2E | S4F | SS1A | SS1B |
|---|---|---|---|---|---|---|
| 1000 | 0.0002 | 0.0000 | 0.0001 | 0.0000 | 0.0001 | 0.0001 |
| 500 | 0.0004 | 0.0002 | 0.0002 | 0.0001 | 0.0001 | 0.0003 |
| 250 | 0.0006 | 0.0003 | 0.0003 | 0.0001 | 0.0002 | 0.0004 |
| 125 | 0.0013 | 0.0005 | 0.0006 | 0.0001 | 0.0005 | 0.0007 |
| 63 | 0.0022 | 0.0011 | 0.0014 | 0.0002 | 0.0012 | 0.0016 |
| 32 | 0.0034 | 0.0017 | 0.0028 | 0.0003 | 0.0023 | 0.0032 |
| 16 | 0.0057 | 0.0026 | 0.0050 | 0.0005 | 0.0048 | 0.0054 |
| 8 | 0.0079 | 0.0031 | 0.0072 | 0.0004 | 0.0068 | 0.0089 |

Plant identification starting with "S" were engineered with the plasmid pCP2 while those starting with "SS" were engineered with pLG3.

Quantification of protein C expression

To confirm results from the first ELISA screening and to obtain a better estimate Of the amount of protein C in transformed plants, an ELISA assay using the above antibodies and sample dilutions was performed. Sap was extracted from each $R_0$ plant selected during the screening, and triplicates of the samples were incubated with the antibodies. Twelve non-transformed plants were used as negative controls to remove background due to plant proteins, and ELISA values were plotted against a purified HPC standard curve. Some $R_0$ plants expressed HPC at almost 0.03% of their proteins, others failed to produce significant amounts (Table 2). The five best plants, S5N, S5R, S2B, SS2D, and S5FF, were selected for a final quantification of HPC and verified for the expression of the NPTII marker gene. The percentage of HPC relative to plant proteins was determined as well as standard deviation.

TABLE 2

Quantification of HPC among $R_0$ plants which were potentially highly expressing protein C

| PLANT | % HPC | STD DEV | PLANT | % HPC | STD DEV |
|---|---|---|---|---|---|
| S5N | 0.028 | 0.001 | S5F | 0.009 | 0.001 |
| S5R | 0.025 | 0.001 | S1B | 0.009 | 0.001 |
| S2B | 0.025 | 0.001 | SS7G | 0.008 | 0.002 |
| SS2D | 0.023 | 0.001 | S1F | 0.008 | 0.001 |
| S5FF | 0.020 | 0.000 | S5W | 0.008 | 0.001 |
| SS7R | 0.019 | 0.001 | S5U | 0.008 | 0.001 |
| SS1A | 0.019 | 0.001 | SS5G | 0.007 | 0.003 |
| S6B | 0.018 | 0.002 | S1I | 0.007 | 0.001 |
| S5B | 0.018 | 0.001 | SS1F | 0.005 | 0.002 |
| S8C | 0.017 | 0.003 | S5CC | 0.004 | 0.002 |
| SS1B | 0.017 | 0.005 | SS4B | 0.004 | 0.000 |

TABLE 2-continued

Quantification of HPC among $R_0$ plants which were potentially highly expressing protein C

| PLANT | % HPC | STD DEV | PLANT | % HPC | STD DEV |
|---|---|---|---|---|---|
| S7L | 0.017 | 0.002 | S4F | 0.003 | 0.001 |
| SS5J | 0.017 | 0.001 | S5H | 0.002 | 0.002 |
| SS3F | 0.016 | 0.000 | S7F | 0.001 | 0.001 |
| S5L | 0.015 | 0.000 | S5X | 0.000 | 0.000 |
| S2F | 0.015 | 0.006 | S7O | −0.000 | 0.002 |
| S5G | 0.014 | 0.001 | SS5B | −0.002 | 0.001 |
| SS8M | 0.014 | 0.003 | S7K | −0.003 | 0.001 |
| SS6B | 0.014 | 0.002 | S6H | −0.003 | 0.002 |
| SS5Q | 0.013 | 0.000 | S5K | −0.005 | 0.001 |
| SS2E | 0.012 | 0.000 | S5I | −0.005 | 0.000 |
| SS6P | 0.011 | 0.002 | | | |

Plant identifications starting with "S" were engineered with the plasmid pCP2 while those starting with "SS" were engineered with pLG3. Readings represent the average of three replicates. "% HPC" is the percent among total soluble tobacco proteins.

Expression of the marker gene NPTII and HPC among the best five plants

The same HPC ELISA procedure as above was used to confirm HPC quantification of the best five HPC-producing tobacco plants. In addition, NPTII ELISA was used to verify the expression of the marker gene. After removing background (PBS-TP buffer) from ELISA readings, all five plants had positive NPTII readings while all four negative control plants had negative NPTII readings (Table 3). Moreover, HPC percentage among soluble proteins was slightly negative for control plants because they consistently had ELISA readings lower than the PBS-TP buffer used to blank readings. Some engineered plants produced 0.02 to 0.03% of HPC. S2B, S5N, S5R, S5FF were transformed with pCP2, SS2D was transformed with pLG3 and C1B, C2A, C3A, C3D were not transformed with a binary vector.

TABLE 3

Percentage of HPC and detection of NPTII from selected $R_0$ plants

| | NPTII READINGS[a] | NPTII STD DEV. | % HPC[b] | HPC STD DEV. |
|---|---|---|---|---|
| S2B | 0.371 | 0.015 | 0.033 | 0.001 |
| S5N | 0.048 | 0.014 | 0.024 | 0.001 |
| S5R | 0.040 | 0.010 | 0.023 | 0.001 |
| SS2D | 0.155 | 0.030 | 0.021 | 0.001 |
| S5FF | 0.134 | 0.050 | 0.020 | 0.002 |
| C1B | −0.079 | 0.017 | −0.008 | 0.001 |
| C2A | −0.101 | 0.018 | −0.007 | 0.001 |
| C3A | −0.152 | 0.007 | −0.010 | 0.001 |
| C3D | −0.084 | 0.002 | −0.004 | 0.003 |

[a]NPTII ELISA readings were blanked against PBS-TP buffer reading.
[b]% HPC is the percentage of HPC among tobacco soluble proteins.
Numbers represent the mean of three replicates.

Expression of HPC in $R_1$ families

The ELISA assay for HPC was used to verify the synthesis of HPC among the progenies of two of the best five HPC-producing tobacco plants. Seeds of S2B, S5N, and C3A were collected and germinated in soil. When $R_1$ plants had approximately four leaves, an ELISA was used to quantify HPC levels (Table 4). Twenty seedlings were tested per mother plant and ratios of seedlings synthesizing HPC versus those not synthesizing HPC were statistically analyzed. Mother plants were S2B and S5N, which were transformed with pCP2. The ratio of S5N progenies expressing HPC to those not expressing HPC was in agreement with the segregation of one dominant gene (Table 4). All S2B progeny expressed HPC, suggesting that two or more T-DNAs were present in the plant genome of the S2B mother plant.

TABLE 4

Inheritance of HPC expression in the $R_1$ generation

| % HPC Detected | S2B[a] | S5N[b] | C3A |
|---|---|---|---|
| 0.02 | 11 | 0 | 0 |
| 0.01 | 9 | 14 | 0 |
| 0.00 | 0 | 6 | 10 |

Numbers represent the number of $R_1$ plants from which 0.02, 0.01, or 0.00% of soluble HPC protein was detected by ELISA.
[a]Chi-square analysis at $p = 0.05$ for the segregation of two or more T-DNA
[b]Chi-square analysis at $p = 0.05$ for the segregation of one T-DNA (3:1).

Double transformation

The S2B tobacco plants used here for a second transformation had previously been screened for their ability to survive on kanamycin medium. It was therefore not possible to use kanamycin selection to identify plants that were transformed a second time, since the same plasmid was used for both transformations. Plants capable of producing larger amounts of HPC (as a result of a second transformation event) were identified by comparing the putative double transformants to three single transformed plants ($F_1$ generation of S-2B plant) for the level of HPC using a DAS-ELISA.

First screen

FIGS. 3 to 6 show the relative HPC content of various second transformants; of 104 plants, eight produced significantly higher amounts of HPC: A 9-4 (#37), B 4-5 (#80), B 5-1 (#81), B 5-2 (#82), B 8-4 (#94), B 9-2 (#97), B 9-4 (#99) and B 10-1 (#100). To avoid eliminating plants that were high producers but were not among the eight best identified above, the 17 best plants (DAS-ELISA units/Bradford units higher than 7) were transferred to the greenhouse for further analysis (indicated by arrows on FIGS. 3 to 6).

Second and third screens

Following two additional quantitative evaluations, three plants showed consistantly higher HPC content: plants B 2-2, B 5-1 and B 8-1. During the second and the third evaluations, their average HPC production were respectively 42% and 23% higher than the three controls.

The plasmid pCP2 contained the marker gene NPTII and the cDNA of HPC under the control of the CaMV 35S promoter. Plasmid pLG3 contained NPTII and the cDNA of HPC was controlled by a dimer of CaMV 35S promoter with an AMV leader sequence. Growing non-transformed tobacco plants on kanamycin-containing medium indicated that the antibiotic selection was efficient while engineering leaf discs with pBI121 showed that the T-DNA was transferred properly to plant cells. The best HPC-producing tobacco plants were shown to express NPTII and HPC at levels representing 0.02 to 0.03% of their soluble proteins. The expression of HPC in $R_1$ plants was transmitted with a 3:1 ratio for S5N progeny while all S2B progeny expressed HPC, suggesting that the mother plant had two or more T-DNA inserts in its genome.

Some plants, transformed a second time, produced more HPC than the original transformants, with the best "twice-transformed" plant producing 43% more than the original mother plant.

5. Partial purification of plant-produced protein C

A series of experiments were designed to partially purify HPC in order to eventually characterize the protein and assay for its activity. All manipulations were performed either on ice or in a cold room at 4° C.

Anion-exchange chromatography

HPC expressed in tobacco plants was partially purified using an affinity chromatography purification protocol. Approximately 10 g of tobacco leaves with positive HPC ELISA readings were homogenized in a Waring™ blender with 30 ml of extraction buffer (20 mM Tris-Cl pH 7.4, 150 mM NaCl, 4 mM EDTA pH 7.4, 5 mM benzamidine-HCl). Most debris was removed by filtration through Miracloth™ and by centrifugation at 15,000 g for 10 minutes. A 16×200 mm column (Pharmacia) was filled with 10 ml of Fast Flow Q™ Sepharose (FFQ) anion exchanger (Pharmacia). FFQ resin was washed with 30 ml of equilibration buffer (20 mM Tris-Cl pH 7.4, 150 mM NaCl, 2 mM EDTA pH 7.4, 2 mM benzamidine-HCl). The sample was applied at the surface of the resin followed by another 30 ml of equilibration buffer. HPC was eluted by injecting 30 ml of elution buffer (20 mM Tris-Cl pH 7.4, 150 mM NaCl, 10 mM $CaCl_2$, 2 mM benzamidine-HCl). A high salt elution was then applied (20 mM Tris-Cl pH 7.4, 400 mM NaCl, 2 mM benzamidine-HCl) and the resin was cleaned with a solution of 2M sodium acetate.

Sephadex desalting

Salts were removed from sap extracts immediately after centrifugation, using PD-10™ columns (Pharmacia) according to the manufacturer's instructions.

Complete debris removal

After centrifugation of the sap extract at 15,000 g, the solution was centrifuged for 1 hour at 100,000 g.

6. Partial purification of plant-produced HPC using ion-exchange chromatography

Following tests to optimize the pH of buffers (as described above in section 5.), three preliminary tests were made on the automated liquid chromatography system (BioRad) in order to set larger scale working conditions.

During experiments, the relative amount of total protein was monitored using the system's UV monitor, whereas the relative amount of HPC was determined on eluted samples using DAS-ELISA. All experiments were conducted under the following conditions:

Samples: Approximately 5.0 g of $HPC^+$ tobacco leaves were homogenized with 15.0 ml of extraction buffer and removed from debris using Miracloth™ and 10 minutes of centrifugation at 15,000 g.

Buffers:

Extraction buffer: 20 mM Tris-Cl, 150 mM NaCl, 4 mM EDTA, 5 mM benzamidine-HCl, pH 8.

Equilibration buffer: 20 mM Tris-Cl, 150 mM NaCl, 2 mM EDTA, 2 mM benzamidine-HCl, pH 5 or 8.

Elution buffer: 20 mM Tris-Cl, 150 mM NaCl, 2 mM benzamidine-HCl, pH 8.

$Ca^{2+}$ elution buffer: 20 mM Tris-Cl, 150 mM NaCl, 10 mM $CaCl_2$, 2 mM benzamidine-HCl, pH 8.

Ion-exchange conditions

Column: Sepharose™ Q (Sigma), 5 ml
Buffers:
 Extraction and equilibration at pH 8
 Elution at pH 8
 10 mM $Ca^{2+}$ elution at pH 8
 10 mM $Ca^{2+}$ salt elution with 200 and 400 mM NaCl at pH 8

7. Analysis of plant-produced HPC
7.1 SDS-PAGE and Western immunoblot

Human Protein C is a 62,000 Da protein made of two subunits (41,000 and 21,000 Da) linked by a disulfide bridge. The addition of mercaptoethanol to the sample before loading onto the gel has the effect of destroying that disulfide bridge. Gel electrophoresis and Western blots were used to characterize the protein produced in tobacco plants.

Western immunoblot

Immunodetection was conducted by blocking 30 minutes with PBS and 5% powdered milk. Rabbit anti-HPC antibody (1:7,000) was added to the blocking solution. After an overnight incubation, the nitrocellulose was washed three times for 10 minutes each with PBS+0.5% Triton™ followed by a 10 minutes wash in TBS. The nitrocellulose was then transferred to TBS+5% powdered milk supplemented with a 1:14,000 dilution of goat anti-rabbit IgG conjugate (Bio-Rad) for 60 minutes. The nitrocellulose was washed four times in TBS for 15 minunutes each. Colorimetric detection of HPC was carried out using alkaline phosphatase activity.

Using these parameters, the samples used were:
S 25 ng of standard HPC (Sigma);
T+ $HPC^+$ tobacco plant (S-2B);
T− $HPC^-$ tobacco plant; and
T++ $HPC^+$ tobacco plant (second transformant).

Figure 7:
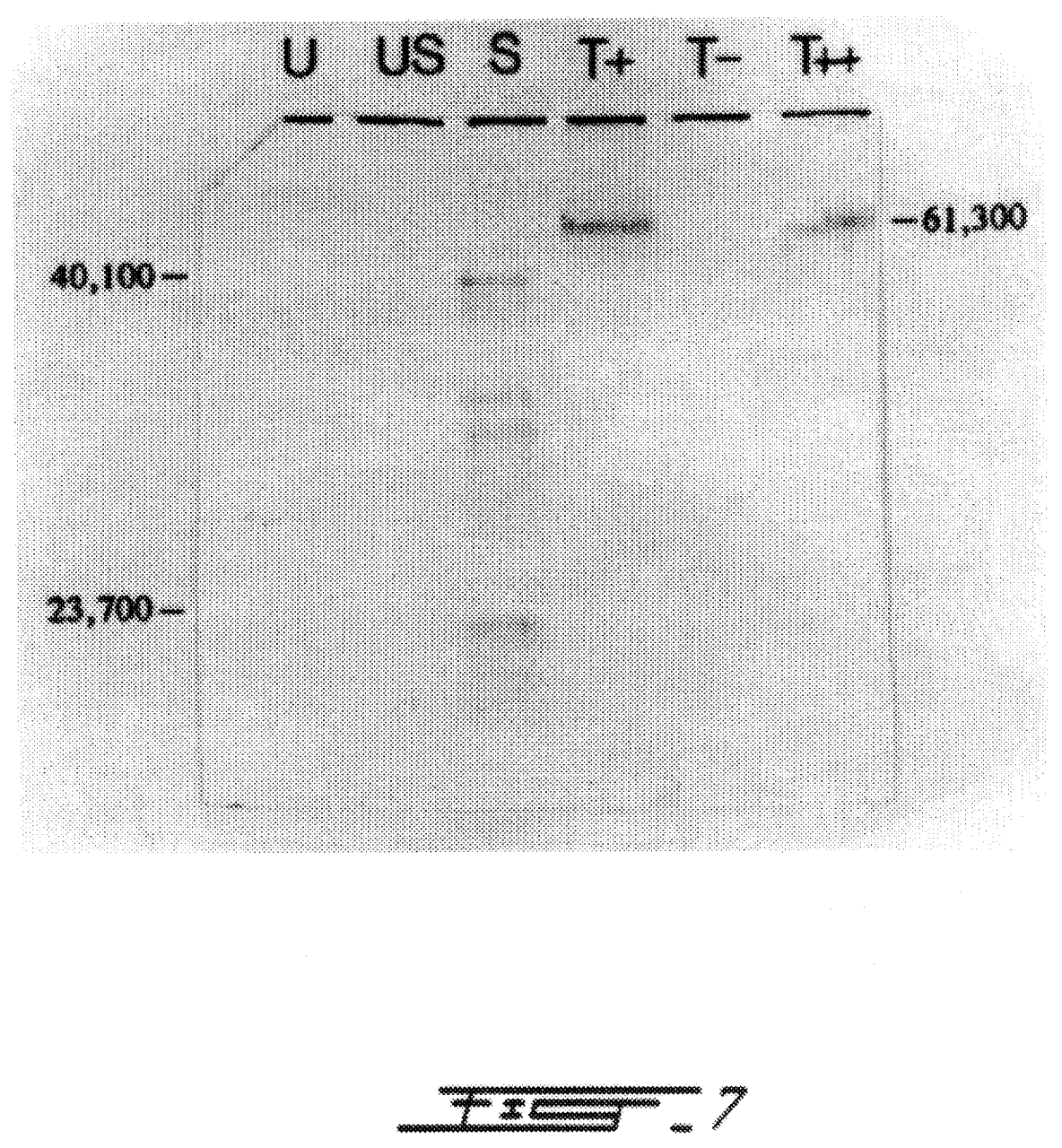

This immunoblot confirmed the presence of HPC in transformed tobacco plants (FIG. 7). Both transformed plants displayed a major protein reacting with anti-HPC serum (lanes T+ and T++:61,300 MW) whereas no band was detected in the control (non-transformed) tobacco plant (lane T−). Lane S contained 25 ng of Sigma HPC. Two major proteins were detected corresponding to the heavy and light chains (40,100 and 23,700 Da, respectively).

From these results, it was concluded that: 1- HPC was produced in transformed plants; 2- HPC was not completely processed and possibly not cleaved into the heavy and light chain.

7.2 HPC location in tobacco plant

HPC concentration was measured in different tissues of a twice-transformed tobacco plant: 1- roots; 2- stem; 3- primary vein of the leaf; 4- leaf without the primary vein. An equal amount of each part of the plant (5.0 g) was homogenized with 15.0 ml of extraction buffer (20 mM Tris, 10 mM benzamidine-HCl, pH 7.4), filtered and centrifuged 10 minutes at 15,000 g. These four extracts were analysed for HPC content using DAS-ELISA.

HPC content of different tissues of tobacco plants was measured using DAS-ELISA. Leaves showed a higher concentration than other parts tested (Table 5). HPC concentration was lowest in the roots.

TABLE 5

| HPC content of various tissues measures using DAS-ELISA | |
|---|---|
| Plant tissue | Amount of HPC (µg HPC/g fresh tissue) |
| Leaves | 0.388 |
| Stem | 0.274 |
| Veins | 0.235 |
| Roots | 0.173 |

7.3 Biological activity using delay in coagulation time

The Acticlot™ assay kit (from American Diagnostica) was used. $HPC^+$ and $HPC^-$ sera, dilution buffer and solutions were prepared according to the manufacturer's instructions. Tubes, Acticlot™ activator and $CaCl_2$ stock solution were prewarmed to working temperature (37° C.).

Prior to testing, HPC samples were prepared as follows: 50 µl undiluted sample, 50 µl HPC deficient plasma, 400 µl American Diagnostica's dilution buffer. A 50 µl volume of this prepared sample was mixed with an equal amount of HPC deficient plasma and incubated for 2 minutes. A volume of 50 µl of Acticlot activator was mixed with the sample solution and incubated five more minutes. Finally, 50 µl of calcium chloride stock solution was added and clotting time was monitored by the tilt-tube technique.

Changes in coagulation times were observed in several experiments when tobacco extracts were tested for clotting activity. Some of the clotting assays indicated that biological activity was present.

TABLE 6

Coagulation times of a tobacco extract using American Diagnostica's Acticlot assay kit

|  | HPC+ | HPC plasma | chromato #9 HPC tobacco | chromato #8 HPC neg. control |
|---|---|---|---|---|
| Assay 1 | 60 sec. | 44 sec. | 52 sec. | 107 sec. |
| Assay 2 | — | — | 145 sec. | 130 sec. |
| Assay 3 | — | — | 40 sec. | 60 sec. |
| Assay 4 | — | — | 140 sec. | 130 sec. |

The present invention will be more readily understood by referring to the following examples which are given to illustrate the invention rather than to limit its scope.

EXAMPLE I

Expression vector pCP2 construction for the production of human protein C

A 1420 bp BclI fragment, which contained the cDNA of HPC, was cut out from pLPC and cloned into the BamHI site of vector pBI524. pBI524 is a derivative of pUC9 with, (5' to 3'), a dimer of the CaMV 35S promoter, an alfalfa mosaic virus (AMV) leader sequence, a polylinker (NcoI, XbaI, BamHI), and a NOS-T. The new construct was called pCP1. In order to verify the orientation of the cloned HPC cDNA, a BglII restriction digestion was performed on plasmid DNA isolated from recovered E. coli colonies. BglII is expected to cleave at the 3' end of the double CaMV 35S promoter and 210 bp away from the 5' end of HPC cDNA thus generating two DNA fragments of approximately 300 bp and 4800 bp if the cDNA was well oriented, that is the ATG codon from the HPC cDNA was immediately downstream of the AMV leader sequence.

An XbaI-EcoRI cassette was isolated from pCP1 and ligated in place of the XbaI-EcoRI cassette from pBI121. Therefore, the GUS gene with the NOS-T was replaced by the cDNA of HPC with its accompanying NOS-T forming the plasmid pCP2. The HPC cDNA is under the control of the constitutive CaMV 35S promoter from pBI121.

Plasmid pCP2 was transferred into A. tumefaciens LBA4404 using the freeze/thaw method. In order to verify whether the plasmids were successfully transferred, a non-radioactive Southern hybridization was performed. The cDNA of HPC was observed to hybridize to plasmid DNA isolated from A. tumefaciens and E. coli.

Seeds of Nicotiana tabacum cv. Xanthi were sterilized for 15 minutes in a 10% bleach solution with a drop of detergent (Tween™-20). Seeds were washed at least five times with sterile distilled water and allowed to germinate and grow on artificial medium composed of the basal MS salts, B5 vitamins, 3% sucrose, and 0.6% agar (Anachemia) at pH 5.7–5.8. Seed were grown under a 16 hour photoperiod with a light intensity of 50 µE and a temperature of 24° C.

A. tumefaciens was grown in Luria Broth (LB) (1% tryptone, 0.5% yeast extract, 85 mM NaCl, pH 7.0) medium supplemented with 50 µg/ml kanamycin and 25 µg/ml of streptomycin for 18 hours or until the optical density at 595 nm reached 0.5 to 1.0. Cells were spun down at 3,000 g for 5 minutes and the pellet was resuspended to its initial volume with MS-104 medium (MS basal salts, B5 vitamins, 3% sucrose, 1.0 µg/ml benzylaminopurine (BAP), 0.1 µg/ml naphtaleneacetic acid (NAA), pH 5.7–5.8, and 0.8% agar) without agar.

Leaf squares of about 64 mm² were dissected using a sharp scalpel, immersed in the inoculum for 15–30 minutes and plated onto MS-104 medium for 2 days under a 16 hour photoperiod, under low light intensity (20 µE) at 24° C. for cocultivation. Leaf discs were washed alternately three times with sterile distilled water for 1 minute and sterile distilled water supplemented with 500 µg/ml of carbenicillin for 5 minutes. Leaf discs were transferred to MS-104 medium with 500 µg/ml of carbenicillin for another 2 days under the same environmental conditions.

Leaf discs were washed as above, plated on MS-104 medium with 500 µg/ml of carbenicillin and 100 µg/ml of kanamycin, and grown using the above environmental conditions until calluses appeared. The light intensity was increased to 50 µE and the explants were allowed to grow until development of well-formed shoots. Shoots were excised and transferred onto MS-rooting medium (MS-104 but with 0.6% agar and no plant growth regulators) with 500 µg/ml of carbenicillin and 100 µg/ml of kanamycin. Surviving plantlets with well-formed roots were removed from the artificial medium, dipped alternately in a 0.06% 50WP Benlate solution and in a rooting powder (Stim-root #1) containing indole-3 butyric acid, and transplanted into pasteurized Promix soil mixture. Plantlets were covered with a transparent cover which was gradually lifted during the following 7 days.

EXAMPLE II

Expression vector pLG3 construction for the production of human protein C

Vector pBI524 contained an undesirable ATG which is part of the NcoI restriction site. The ATG was deleted by cleaving pBI524 with NcoI, removing single stranded sticky ends with mung bean nuclease, and ligating the modified vector which was named pLG1. The removal of the NcoI restriction site was verified with a double digestion with NcoI and ScaI. Two bands were observed when pBI524 was digested with the two restriction enzymes while only one band appeared for pLG1 indicating that the NcoI site was missing.

The HPC cDNA BclI fragment was cloned into the BamHI site of pLG1 to create pLG2. Then, a HindIII-EcoRI cassette from pLG2 was cloned in place of the HindIII-EcoRI from pBI121. Therefore, the CaMV 35S promoter along with the GUS gene and a NOS-T were replaced by a dimer of the CaMV 35S promoter with an AMV leader sequence, the cDNA of HPC, and a NOS-T.

Plasmid pLG3 was transferred into A. tumefaciens LBA4404 using the freeze/thaw method. In order to verify whether the plasmids were successfully transferred, a non-radioactive Southern hybridization was performed. The cDNA of HPC was observed to hybridize to plasmid DNA isolated from A. tumefaciens and E. coli.

Seeds of Nicotiana tabacum cv. Xanthi were sterilized for 15 minutes in a 10% bleach solution with a drop of detergent (Tween™-20). Seeds were washed at least five times with sterile distilled water and allowed to germinate and grow on artificial medium composed of the basal MS salts, B5 vitamins, 3% sucrose, and 0.6% agar (Anachemia) at pH 5.7–5.8. Seed were grown under a 16 hour photoperiod with a light intensity of 50 µE and a temperature of 24° C.

A. tumefaciens was grown in Luria Broth (LB) (1% tryptone, 0.5% yeast extract, 85 mM NaCl, pH 7.0) medium supplemented with 50 µg/ml kanamycin and 25 µg/ml of streptomycin for 18 hours or until the optical density at 595 nm reached 0.5 to 1.0. Cells were spun down at 3,000 g for 5 minutes and the pellet was resuspended to its initial volume with MS-104 medium (MS basal salts, B5 vitamins, 3% sucrose, 1.0 µg/ml benzylaminopurine (BAP), 0.1 µg/ml naphtaleneacetic acid (NAA), pH 5.7–5.8, and 0.8% agar) without agar.

Leaf squares of about 64 mm$^2$ were dissected using a sharp scalpel, immersed in the inoculum for 15–30 minutes and plated onto MS-104 medium for 2 days under a 16 hour photoperiod, under low light intensity (20 µE) at 24° C. for cocultivation. Leaf discs were washed alternately three times with sterile distilled water for 1 minute and sterile distilled water supplemented with 500 µg/ml of carbenicillin for 5 minutes. Leaf discs were transferred to MS-104 medium with 500 µg/ml of carbenicillin for another 2 days under the same environmental conditions.

Leaf discs were washed as above, plated on MS-104 medium with 500 µg/ml of carbenicillin and 100 µg/ml of kanamycin, and grown using the above environmental conditions until calluses appeared. The light intensity was increased to 50 µE and the explants were allowed to grow until development of well-formed shoots. Shoots were excised and transferred onto MS-rooting medium (MS-104 but with 0.6% agar and no plant growth regulators) with 500 µg/ml of carbenicillin and 100 µg/ml of kanamycin. Surviving plantlets with well-formed roots were removed from the artificial medium, dipped alternately in a 0.06% 50WP Benlate solution and in a rooting powder (Stim-root #1) containing indole-3 butyric acid, and transplanted into pasteurized Promix soil mixture. Plantlets were covered with a transparent cover which was gradually lifted during the following 7 days.

EXAMPLE III

Expression vector construction for the production of chicken nuclear oncoprotein p53

Proceeding as for Example I, but using a cDNA sequence coding for chicken nuclear oncoprotein p53 instead of the cDNA of the human protein C gene.

Vector pBI524 contained an undesirable ATG which is part of the NcoI restriction site. The ATG was deleted by cleaving pBI524 with NcoI, removing single stranded sticky ends with mung bean nuclease, and ligating the modified vector which was named pLG1. The removal of the NcoI restriction site was verified with a double digestion with NcoI and ScaI. Two bands were observed when pBI524 was digested with the two restriction enzymes while only one band appeared for pLG1 indicating that the NcoI site was missing.

The chicken cDNA for nuclear oncoprotein p53 is excised using EcoRI restriction digestion. T4 DNA polymerase is used to fill in the 3' recessed end and therefore eliminate the EcoRI site. BamHI linkers (5'-CGGATCCG-3') are added by ligation with T4 DNA ligase. The BamHI ends are then digested with BamHI and ligated into the BamHI site of pLG1 to create pLG53. Then, a HindIII-EcoRI cassette from pLG2 is cloned in place of the HindIII-EcoRI from pBI121.

Therefore, the CaMV 35S promoter along with the GUS gene and a NOS-T were replaced by a dimer of the CaMV 35S promoter with an AMV leader sequence, the cDNA of HPC, and a NOS-T. Plasmids pLG53 is transferred into A. tumefaciens LBA4404 using the freeze/thaw method.

Seeds of Nicotiana tabacum cv. Xanthi are sterilized for 15 minutes in a 10% bleach solution with a drop of detergent (Tween™-20). Seeds are washed at least five times with sterile distilled water and allowed to germinate and grow on artificial medium composed of the basal MS salts, B5 vitamins, 3% sucrose, and 0.6% agar (Anachemia) at pH 5.7–5.8. Seed are grown under a 16 hour photoperiod with a light intensity of 50 µE and a temperature of 24° C.

A. tumefaciens is grown in Luria Broth (LB) (1% tryptone, 0.5% yeast extract, 85 mM NaCl, pH 7.0) medium supplemented with 50 µg/ml kanamycin and 25 µg/ml of streptomycin for 18 hours or until the optical density at 595 nm reaches 0.5 to 1.0. Cells are spun down at 3,000 g for 5 minutes and the pellet is resuspended to its initial volume with MS-104 medium (MS basal salts, B5 vitamins, 3% sucrose, 1.0 µg/ml benzylaminopurine (BAP), 0.1 µg/ml naphtaleneacetic acid (NAA), pH 5.7–5.8, and 0.8% agar) without agar.

Leaf squares of about 64 mm$^2$ are dissected using a sharp scalpel, immersed in the inoculum for 15–30 minutes and plated onto MS-104 medium for 2 days under a 16 hour photoperiod, under low light intensity (20 µE) at 24° C. for cocultivation. Leaf discs are washed alternately three times with sterile distilled water for 1 minute and sterile distilled water supplemented with 500 µg/ml of carbenicillin for 5 minutes. Leaf discs are transferred to MS-104 medium with 500 µg/ml of carbenicillin for another 2 days under the same environmental conditions.

Leaf discs are washed as above, plated on MS-104 medium with 500 µg/ml of carbenicillin and 100 µg/ml of kanamycin, and grown using the above environmental conditions until calluses appeared. The light intensity is increased to 50 µE and the explants allowed to grow until development of well-formed shoots. Shoots are excised and transferred onto MS-rooting medium (MS-104 but with 0.6% agar and no plant growth regulators) with 500 µg/ml of carbenicillin and 100 µg/ml of kanamycin. Surviving plantlets with well-formed roots are removed from the artificial medium, dipped alternately in a 0.06% 50WP Benlate solution and in a rooting powder (Stim-root #1) containing indole-3 butyric acid, and transplanted into pasteurized Promix soil mixture. Plantlets are covered with a transparent cover which is gradually lifted during the following 7 days.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. An expression vector for the large scale production of human or animal protein, which comprises a DNA construct consisting of operatively linked DNA coding for a plant promoter, a mRNA stabilizer, a transcription terminator and said human or animal protein to be expressed, wherein the human or animal protein is a protein chosen from a family of proteins, wherein said family of proteins is selected from the group consisting of colony stimulating factors, relaxins, polypeptide hormones, growth factors and coagulation factors, wherein said expression vector is pCP2.

2. An expression vector for the large scale production of a human or animal protein, which comprises a DNA construct consisting of operatively linked DNA coding for a plant promoter, a mRNA stabilizer a transcription terminator and said human or animal protein to be expressed, wherein said human or animal protein is selected from the group of proteins consisting of human protein C (HCP), factor VIII, growth hormone, erythropoietin, interleukin 1, interleukin 2, interleukin 3, interleukin 4, interleukin 5, interleukin 6, and interleukin 7, wherein said expression vector is pCP2.

3. An expression vector for the large scale production of a human or animal protein, which comprises a DNA construct consisting of operatively linked DNA coding for a plant promoter, a mRNA stabilizer, a transcription terminator, and said human or animal protein to be expressed, wherein the human or animal protein is a protein chosen from a family of proteins, wherein said family of proteins is selected from the group consisting of colony stimulating factors, relaxins, polypeptide hormones, cytokines, growth factors and coagulation factors, wherein said expression vector is pLG3.

4. An expression vector for the large scale production of a human or animal protein, which comprises a DNA construct consisting of operatively linked DNA coding for a plant promoter, a mRNA stabilizer, a transcription terminator, and said human or animal protein to be expressed, wherein said human or animal protein is selected from the group of proteins consisting of human protein C (HPC), factor VIII, growth hormone, erythropoietin, interleukin 1, interleukin 2, interleukin 3, interleukin 4, interleukin 5, interleukin 6, and interleukin 7, wherein said expression vector is pLG3.

5. A plant bioreactor for the large scale production of human or animal protein, which comprises dicotyledonous plants transformed with the expression vector of claim 2 which further includes a suitable selectable marker for plant transformation.

6. The plant bioreactor of claim 5, wherein said suitable selectable marker is kanamycin resistance.

7. A plant bioreactor for the large scale production of a human or animal protein, which comprises dicotyledonous plants transformed with the expression vector of claim 4, which further includes a suitable selectable marker for plant transformation.

8. The plant bioreactor of claim 7 wherein said suitable selectable marker is kanamycin resistance.

9. A method of large scale production of human protein C, which comprises the steps of:

a) inserting the recombinant expression vector pCP2 of claim 2 into a plant cell using Agrobacterium transformation, said expression vector comprising operatively linked DNA coding for a plant promoter, a transcription terminator and said human protein C to be expressed flanked by T-DNA borders and a suitable selectable marker for plant transformation, whereby the plant cell becomes a transformed plant cell; and b) extracting said expressed human protein C from said transformed plant cell.

10. The method of claim 9, wherein said suitable selectable marker is kanamycin resistance.

11. A method of large scale production of human protein C, which comprises the steps of:

a) inserting the recombinant expression vector pLG3 of claim 4 into a plant cell using Agrobacterium transformation, said expression vector comprising operatively linked DNA coding for a plant promoter, a mRNA stabilizer, a transcription terminator, and said human protein C to be expressed flanked by T-DNA borders and a suitable selectable marker for plant transformation, whereby the plant cell becomes a transformed plant cell; and b) extracting said expressed human protein C from said transformed plant cell.

12. The method of claim 11, wherein said suitable selectable marker is kanamycin resistance.

* * * * *